United States Patent

Rousseau et al.

[19]

[11] Patent Number: 6,044,126
[45] Date of Patent: Mar. 28, 2000

[54] PROCESS FOR AUTOMATICALLY DETERMINING THE CONFIGURATION OF A STEREOTACTIC RADIOSURGERY HELMET TO WHICH CAN BE FITTED A PLURALITY OF COLLIMATORS FOCUSED ON AN IRRADIATION ISOCENTER

[75] Inventors: Jean Rousseau; David Gibon, both of Lille, France

[73] Assignees: CH&U de Lille; Centre Oscar Lambret-Centre Regional de Lutte Contre, both of Lille Cedex, France

[21] Appl. No.: 09/102,216

[22] Filed: Jun. 22, 1998

[30] Foreign Application Priority Data

Jun. 23, 1997 [FR] France ................................. 97 08064

[51] Int. Cl.$^7$ ..................................................... A61N 5/10
[52] U.S. Cl. .................. 378/65; 378/148; 600/1
[58] Field of Search .................. 378/64, 65, 68, 378/148, 150; 600/1

[56] References Cited

U.S. PATENT DOCUMENTS

| | | |
|---|---|---|
| 4,780,898 | 10/1988 | Sundqvist . |
| 5,315,360 | 5/1994 | Sturm et al. . |
| 5,602,892 | 2/1997 | Llacer ........................................ 378/65 |
| 5,627,870 | 5/1997 | Kopecky ................................... 378/65 |
| 5,629,967 | 5/1997 | Leksell et al. ............................ 378/65 |
| 5,647,663 | 7/1997 | Holmes . |

FOREIGN PATENT DOCUMENTS

| | | |
|---|---|---|
| 0 560 331 A1 | 9/1993 | European Pat. Off. . |
| 91 01279 | 8/1992 | France . |
| WO 97 28845 | 8/1997 | WIPO . |

*Primary Examiner*—David P. Porta
*Attorney, Agent, or Firm*—Wolf, Greenfield & Sacks, P.C.

[57] ABSTRACT

Process for determining the configuration or configurations [treatment time ($TT_i$)/diameter ($\phi_{i,j}$) of each collimator] of a helmet for stereotactic radiosurgery, to which can be fitted an plurality of collimators focused on an irradiation isocenter, consisting in automatically optimizing, through iterative dose calculation, the dose ($D_p$) received at predetermined optimization points ($M_p$), by modifying, in the course of the successive iterations, the treatment time ($TT_i$) of at least one shot (i) and the diameter ($\phi_{i,j}$) of at least one collimator ($C_j$) of at least one shot (i), and by calculating, at each iteration, an objective function (OF) having as variables the differences between the calculated dose ($D_p$) and the expected dose ($ED_p$) for each point of optimization ($M_p$), iterative calculation of the doses being carried out automatically until the objective function (OF) satisfies a predetermined optimization criterion.

10 Claims, 2 Drawing Sheets

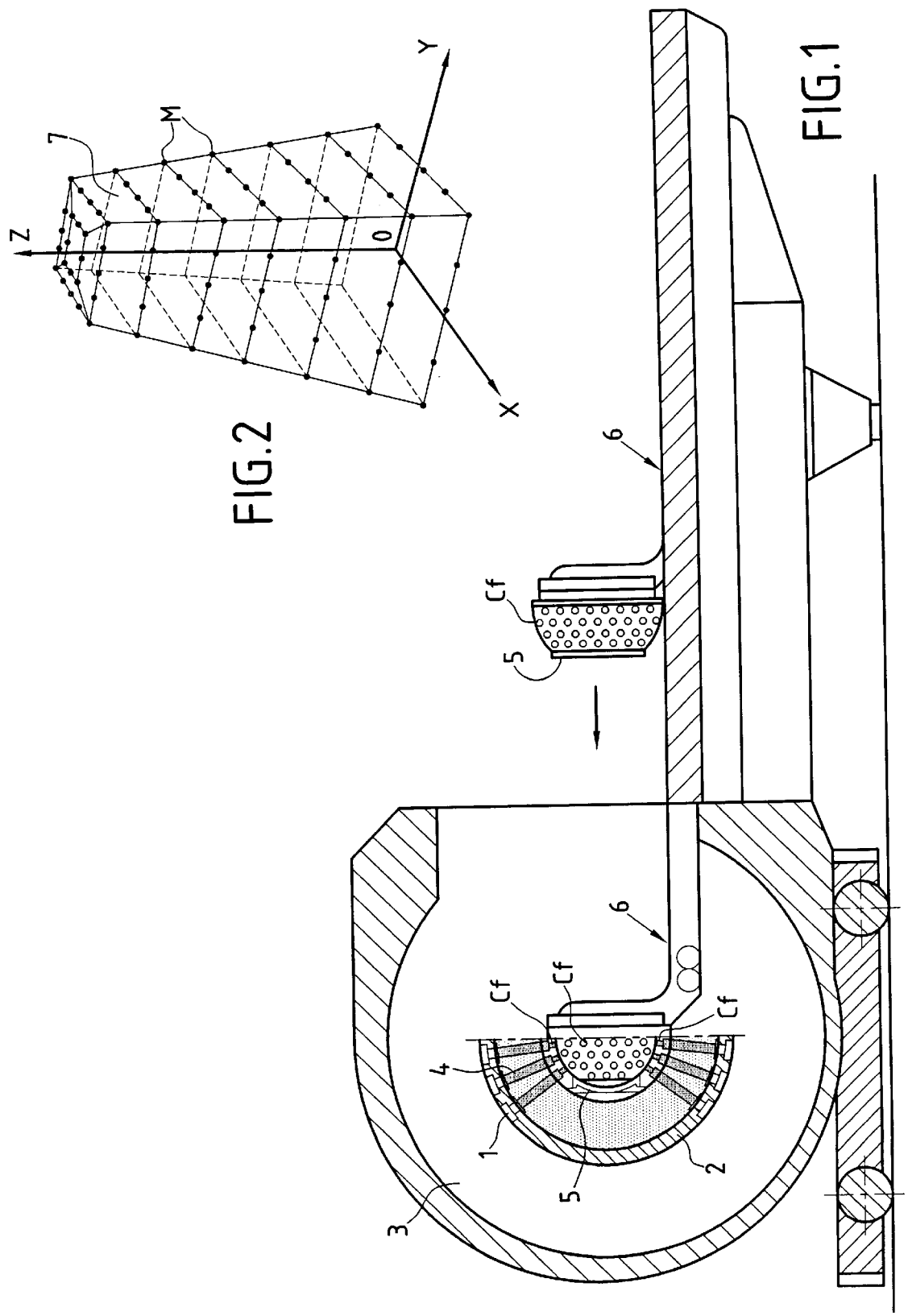

PROCESS FOR AUTOMATICALLY DETERMINING THE CONFIGURATION OF A STEREOTACTIC RADIOSURGERY HELMET TO WHICH CAN BE FITTED A PLURALITY OF COLLIMATORS FOCUSED ON AN IRRADIATION ISOCENTER

FIELD OF THE INVENTION

The present invention relates to the field of stereotactic radiosurgery and, more precisely, to radiation therapy for small brain lesions by means of a device making use of a helmet to which can be fitted a plurality of interchangeable, static collimators focused on one and the same irradiation isocenter. It relates more especially, to a process for automatically determining the helmet configuration, or successive helmet configurations, (the diameter of each collimator and the treatment time) according to whether the subsequent treatment plan is of the single-target or multi-target plan.

BACKGROUND OF THE INVENTION

Generally speaking, stereotactic radiosurgery is concerned with radiation therapy for small intracranial volumes and, for example, for arteriovenous malformations, or for tumors. It makes use chiefly, at the present time, of two different techniques that have proved their worth for many years, a dynamic technique and a static technique.

The dynamic technique involves a single source capable of producing a narrow beam of ionizing radiation that is mobile in space in relation to the target volume to be treated.

This first technique makes use of devices mainly constructed on the basis of linear accelerators, and ionizing radiation is mostly produced by a source of high-energy photons.

The static technique makes involves a plurality of ionizing beams which, during treatment, are static in relation to the target volume to be treated, being sharply collimated and focused on one and the same irradiation isocenter. The invention falls within the field of the aforementioned second, static technique, which will now be described in greater detail.

A stereotactic radiosurgery device using the static technique has already been described, for example, in French patent application FR 2 672 220 and in U.S. Pat. No. 4,780,898. Such a device comprises a plurality of sources of ionizing radiation and, for example, radioactive sources of gamma radiation, of the $^{60}Co$ sources, which are mounted on a hemispherical device facing a plurality of primary collimators, there being one source for each primary collimator. A helmet internal to the aforementioned hemispherical device is fitted with smaller diameter secondary, removable collimators and enables a plurality of isocentric mini-beams to be obtained.

Prior to implementing the treatment, a stereotactic frame is placed on the patient's skull, this frame serving to locate the volume to be treated, known as the 'target volume', in the mechanical coordinate system of the treatment device, using an appropriate medical imaging modality (essentially, X-ray angiography for arteriovenous malformations and Computed Tomography or Magnetic Resonance Imaging in the case of tumoral lesions). The same stereotactic frame is used to position the patient's skull in relation to the helmet of the stereotactic radiosurgery device, in such a way that the irradiation isocenter of the helmet is in a known position in relation to the target volume.

To effect a shot at a given point on the target volume, known as the 'target point', the patient's skull is positioned in such a way that the irradiation center of the helmet coincides with the target point. When all the collimators on the helmet are of the same diameter, the spatial distribution of the dose obtained in a volume assumed to be homogenous is substantially spherical and centered on the isocenter, the maximum dose being delivered at the isocenter, and the dose delivered at a distance from the isocenter equal to the radius of the collimators substantially amounting to 50% of the maximum dose received by the isocenter. In the static radiosurgery technique, the treatment of a target volume is thus comparable with a punching out operation, during which it is attempted to juxtapose spatially the doses delivered at each shot in such a way as to cover the target volume in its entirety.

In usual practice, as a function of a predetermined target volume for treatment, an operator specialized in radiosurgery decides on a treatment plan, by defining, in a first stage, the number of shots to be effected, and the target point of each shot, that is to say the point on the target volume on which, for a given shot, the irradiation center has to be positioned, and, in a second stage, the configuration of the helmet for each shot. The configuration of the helmet is to be taken here as referring to the diameter of the secondary collimators that have to be mounted on the helmet, and the treatment time for a given shot, that is to say the duration of the shot. The operator can thus decide that a single-target plan, that is to say a single shot on a single target point, is sufficient, if he considers that a single shot will enable a sufficient dose to be delivered throughout the target volume, or, on the contrary, decide on a multi-target plan, effecting a series of successive shots on predetermined target points. The treatment plan and the configuration, or successive configurations, of the helmet must be chosen not only in order to cover the entire target volume with the optimum treatment dose, but also, when the target volume is positioned in the vicinity of a sensitive area, for example in the vicinity of the optic chiasma, taking care to ensure that the dose delivered in this sensitive area, and, generally speaking, outside the target volume, be as small as possible. For this purpose, the operator takes as his basis a certain number of predetermined points for which he knows the optimum dose that ought to be delivered at each of these points these will be, for example, points on the envelope of the target volume, certain points on the inside of the target volume, and, if applicable, certain sensitive points placed outside and in the vicinity of the target volume, and for which the dose must be as small as possible.

Hitherto, and in practice, a specialized operator has had several helmets with which to define his treatment plan, each helmet comprising a number of collimators equal to the number of collimators that can be fitted on the helmet. The collimators for each helmet are of identical or different diameters from one helmet to another. The configuration of the helmet for each shot (diameter of the collimators on the helmet and shot duration) is determined empirically. In order, as a preliminary measure, to validate his choice of configurations and, if applicable, to change it, the operator is provided with a software that enables him, on the basis of each helmet configuration, to effect automatically a three-dimensional calculation of the dose resulting from the set of shots in the case of a multi-target plan, or from a single shot in the case of a single-target plan. The relevance of the configurations for a given treatment plan is gauged by comparing the three-dimensional distribution of the calculated dose with the target volume and, as applicable, with the sensitive volumes.

There are several drawbacks in empirically choosing helmet configurations. The choice necessarily has to be made by an operator specialized in radiosurgery, on the basis of his experience. It leads, in practice, to a three-dimensional dose geometry which is not best suited to the target volume, which target volume can have any non-spherical contour; as a result, to cover the target volume in its entirety while, at the same time, avoiding, as far as possible, irradiating the area of healthy tissue in the external vicinity of the target volume, the operator has, in practice, to carry out, almost systematically, a series of several shots, knowing that he has a limited choice of collimator diameters. Now, each shot necessitates considerable time for treatment and for positioning the patient, which leads to substantial operating overheads and discomfort to the patient. From a financial viewpoint, and to ensure the patient's comfort, it thus proves necessary to limit the number of shots, and even to be able to reduce the treatment plan to a single shot.

SUMMARY OF THE INVENTION

The invention aims to provide a process for determining the configuration, or successive configurations, of a static stereotactic radiosurgery helmet which overcomes the aforementioned drawbacks. It is based on a process which, on one hand, is designed to be implemented automatically by a suitably programmed calculator, and which, as a result, no longer necessitates any action by a specialized operator, and which, on the other hand, makes it possible to determine helmet configurations for which the collimator dimensions are different for one and the same helmet in such a way that the three-dimensional geometry of the dose delivered is better suited to the target volume. The main advantage as regards treatment is that it is possible to reduce the number of shots.

According to the process of the invention, on the basis:
of optimization points ($M_p$) chosen in relation to the target volume,
of an expected irradiation dose ($ED_p$) at each optimization point ($M_p$),
and of one (a single shot) or several (a series of successive shots) predetermined initial helmet configurations,
the dose ($D_p$) received at each optimization point ($M_p$) is automatically optimized, through iterative dose calculation, by modifying, in the course of the successive iterations, the treatment time ($TT_i$) of at least one shot (i), and the diameter ($\phi_{i,j}$) of at least one collimator ($C_f$) used for at least one shot (i), and by calculating, at each iteration, an objective function (OF) having as variables the differences between the calculated dose ($D_p$) and the expected dose ($ED_p$) for each point of optimization ($M_p$), iterative calculation of the doses being carried out automatically until the objective function (OF) satisfies a predetermined optimization criterion.

Prior to the invention, it had already been proposed to replace certain collimators on a helmet by plugs, for the purpose of locally cutting off one or more isocentric irradiation beams and, by this expedient, of modeling the isodose contour around the irradiation isocenter. However, the method of determining the helmet configurations remained empirical, and was still practiced by a specialized operator, and there has never been any attempt, to date, to combine, on one and the same helmet, collimators having non-zero diameters of aperture that were different.

Generally speaking, within the framework of the invention, the notion of a collimator covers both collimators having a non-zero diameter of aperture and plugs which, for the purposes of generalization are likened to collimators the diameter of which is zero.

BRIEF DESCRIPTION OF THE DRAWINGS

Further characteristics of the process according to the invention will emerge more clearly from a study of the detailed description that follows of a preferred exemplary form of embodiment, which description is given by way of a non-limitative example, and with reference to the annexed drawings, wherein:

FIG. 1 is a diagrammatic representation of a known stereotactic radiosurgery device, corresponding to the static technique;

FIG. 2 illustrates an example of the geometry of an intracranial target volume to be treated.

DETAILED DESCRIPTION OF THE PREFERRED EMBODIMENT

Figure 3:
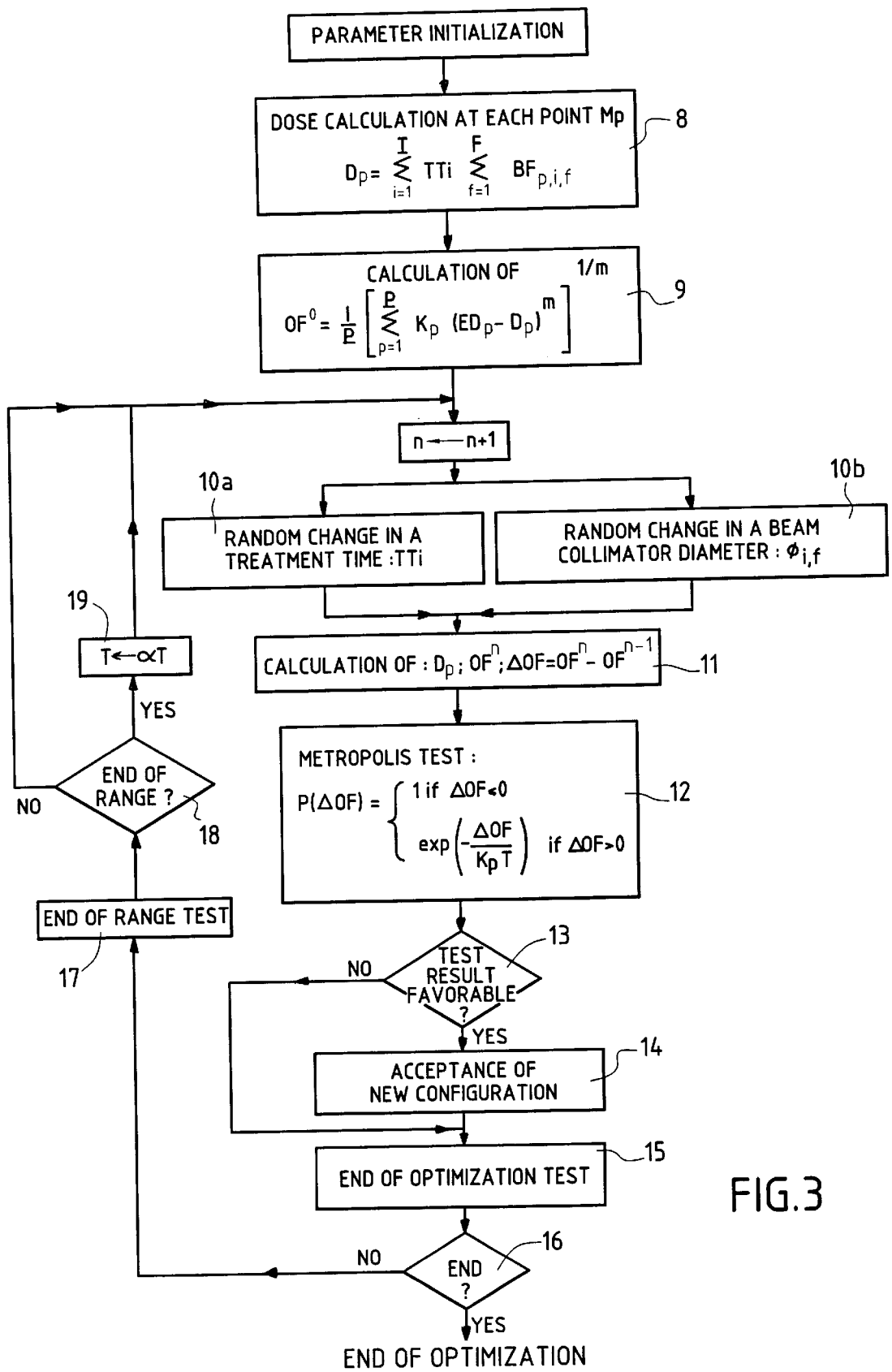
FIG. 3 is a flow diagram illustrating the main steps in a particular example of automatic implementation of the process according to the invention.

With reference to FIG. 1, a stereotactic radiosurgery device for the treatment of cerebral lesions (arteriovenous malformations or tumors), corresponding to the static technique, includes a plurality of sources, 1, of ionizing radiation, which are arranged, statically, on a hemispherical device, 2, housed inside a shielded cavity, 3, forming a radiation shield, and a helmet, 5, designed to be received inside hemispherical device 2. The latter comprises, for each source 1, a primary collimator, 4, communicating with source 1. Helmet 5 is designed to carry a plurality of isocentric secondary collimators, $C_f$, which are interchangeable, and which, once helmet 5 is housed inside hemispherical device 2, take up positions respectively facing primary collimators 4. Once helmet 5 is in position inside hemispherical device 2, sources 1 emit ionizing radiation in the form of a plurality of mini-beams which are collimated by primary collimators 4 and secondary collimators $C_f$, and which are centered on one and the same irradiation isocenter.

Before helmet 5 is placed on the skull of a patient, a stereotactic frame (not shown) is fitted to the patient in the usual way, this frame making it possible, in an initial stage, to locate, in the mechanical reference system of the radiosurgery device, the intracranial target volume to be treated, using a suitable medical imaging modality. This can involve, for example, X-ray angiography, in the case of arteriovenous malformations, and Computed Tomography or Magnetic Resonance Imaging, in that of tumoral lesions. In a second stage, with the patient lying on table 6 of the radiosurgery device, the stereotactic frame is used to position the patient's skull in relation to helmet 5, in such a way that the irradiation isocenter is centered on a predetermined target point on the target volume to be treated. Once this positioning operation has been completed, the radiosurgery helmet 5 fixed to the patient's skull is translated in the direction of hemispherical device 2, until helmet 5 is in position inside hemispherical device 2.

By way of a non-limitative example, the radiosurgery device of FIG. 1 was constituted by 201 sources of $^{60}$Co, the initial activity of which was 1.1 $10^{12}$ Bq. These sources were arranged on hemispherical device 2 facing 201 157 mm long primary collimators 4. Helmet 5 had a diameter of 40 cm, and was capable of carrying 201 60 mm long cylindrical secondary collimators $C_f$. Each secondary collimator $C_f$ could have a collimating diameter of 4, 8, 14 or 18 mm. Plugs could also be mounted on helmet 5 in place of the secondary collimators, so as to cut off certain irradiation beams. In what follows, these plugs will be considered as constituting secondary collimators of zero diameter. Helmet 5 thus enabled a maximum of 201 isocentric mini-beams of gamma photons, of 1.17 MeV and 1.33 MeV, emitted by the sources of $^{60}$Co, to be obtained. The invention is not, however, limited to a stereotactic radiosurgery device using radioactive sources of gamma radiation of the $^{60}$Co source type, and can be applied to any type of stereotactic radiosurgery device which, generally speaking, uses a plurality of isocentric mini-beams of ionizing radiation. This could include, for example, X-rays, proton, neutron or electron radiation.

FIG. 2 shows a particular example of three-dimensional geometry of an intracranial target volume 7 that can be treated using the device of FIG. 1, and located in the mechanical reference system (Ox, Oy, Oz) of the radiosurgery device. In FIG. 2, volume 7 is represented by a plurality of points M delimiting the envelope of target volume 7.

Before helmet 5 is placed on the patient, with a view to subsequently treating a given intracranial target volume, a specialized operator decides, in a first stage, as to the number of shots that will have to be effected, and as to the target point of each shot, that is to say the point on the target volume on which, for a given shot, the irradiation isocenter of helmet 5 has to be positioned. The method of determining the positions of the target points can take the form of empirically trying to ensure optimum coverage of the target volume by a certain number of spheres (one sphere per shot) of different diameters. Each sphere substantially corresponds to the volume that would be irradiated by a shot by means of a helmet 5 on which were mounted only all the secondary collimators of the same diameter. It should also be noted that this method of determining the target points can also be carried out automatically, using suitable software. As this automatic method is known from other sources, it will not be discussed in detail in the present description. It would simply be pointed out that this automatic method resides in optimization of the placing and of the diameters of the spheres by an algorithm of conjugate gradients making it possible to minimize the following objective function $$OF = \frac{1}{N}\sum_{n=1}^{N}(d_{n,s})^2$$

where:

N is the number of points M ($x_n$, $y_n$, $z_n$) on the envelope of the target volume, and $d_{n,B}=(x_n-x_B)^2+(y_n-y_B)^2+(z_n-z_B)^2-a_B^2$, with ($x_B$, $y_B$, $z_B$) and $a_B$ representing, respectively, the co-ordinates of the center and the radius of each sphere.

Once the number of shots and the target points of each shot have been determined, it is necessary, in a second stage, to determine the configuration, or successive configurations, of helmet 5, that is to say, for each shot, the diameters of the secondary collimators $C_f$ that have to be mounted on helmet 5, and the treatment time, that is to say the duration of the shot.

Hitherto, this second stage was necessarily carried out empirically by the specialized operator on the basis of a number of predetermined points for which the operator knew the optimum dose that would have to be delivered at each of these points.

The process according to the invention advantageously enables this second stage to be replaced by a process for automatically determining the configuration, or successive configurations, of the helmet, based on an algorithm for optimization through iterative dose calculation, which can be implemented by suitably programming any known computer. One particular example of the use of this optimization algorithm will now be described with reference to the flow diagram in FIG. 3.

The main parameters of the flow diagram in FIG. 3 are as follows $M_p$ ($x_p$, $y_p$, $z_p$): optimization points P: number of optimization points $K_p$: weighting factor assigned to each point ($M_p$)

$ED_p$: expected dose at an optimization point ($M_p$)

$D_p$: calculated dose at the optimization point ($M_p$)

I: number of shots i: shot number (with i ranging from 1 to I)

$TT_i$: treatment time for one shot (i)

F: maximum number of beams for a helmet f: helmet beam number (with f ranging from 1 to F)

$\phi_{i,f}$: diameter of the collimator of the beam (f) of the shot (i)

$BF_{p,i,f}$: dose beam factor that is assigned to each beam (f) of a shot (i), for a given optimization point ($M_p$), and which is calculated according to the position of the beam (f) in relation to the optimization point ($M_p$), taking into account the diameter $\phi_{i,f}$ of the collimator corresponding to the beam f and the associated physical data Kp: Boltzmann's constant T: control parameter (temperature) of the Metropolis test.

Among the above parameters, the optimization points $M_p$ are points determined by the specialized operator, on the basis of the target volume to be treated. These optimization points are constituted, in practice, by a certain number of points M on the envelope of the target volume to be treated, to which can be added particular points chosen inside the target volume, and points located outside the target volume and corresponding to sensitive volumes for which it is preferable to limit irradiation doses. For each of these optimization points $M_p$ is defined an expected optimum irradiation dose $ED_p$. A weighting factor $K_p$ is assigned to each optimization point according to the importance that the specialized operator wishes to ascribe to this point. In other words, the more the specialized operator thinks it important that the irradiation dose that will actually be delivered at this point should be the closest possible to the expected dose, with the helmet configuration, or successive configurations, which have been previously determined automatically, the more this coefficient will be important by comparison with the coefficients assigned to the other optimization points.

Prior to implementing the optimization algorithm according to the flow diagram in FIG. 3, all of the beam factors $BF_{p,i,f}$ that are assigned, for each optimization point $M_p$, to each beam f of a shot i are calculated as a function of the position of the associated beam f in relation to optimization point $M_p$, that is to say, in particular, as a function of the position of the target point (the irradiation isocenter of the helmet) in relation to the corresponding optimization point $M_p$, and taking into account the diameter $\phi_{i,f}$ of the collimator corresponding to the beam (f) and the associated physical data, such as, for example, the depth of penetration of the beam at point $M_p$. This beam factor quantifies the contribution of beam f in the irradiation dose that will be received by optimization point $M_p$. In the case of a secondary collimator of zero diameter (a plug), the corresponding beam factor will be zero. Such calculation of the beam factors is known per se and will not, therefore, be described in detail herein. For further information on beam factor calculation, readers are referred to the following publication: Phillips MII: Physical aspects of stereotactic radiosurgery, New York, Plenum Publishing Corporation, 1993.

These beam factors pre-calculated for each beam f and each optimization point $M_p$ will be saved in a table of values which will be accessed automatically during the dose calculation stage, which will make it possible, at the time of implementing the flow diagram of FIG. 3, to avoid having to calculate beam factors, which is costly in terms of computing time.

The different steps of the flow diagram in FIG. 3 will now be discussed. The flow diagram in FIG. 3 is essentially based on an iterative dose calculation DP according to the known formula featuring in block 8 of the flow diagram, and on the evaluation, at each iteration (n), of the value $OF^n$ of an objective function OF according to the formula given in block 9 of the said flow diagram. In this formula, the variable m will be positive which, in a preferred alternative form of embodiment, was fixed at 2.

Initially, one starts out from one or more predetermined initial helmet configurations, depending on whether a single-target or multi-target plan has been decided on. For this purpose, variables $TT_i$ will be initialized to some initial value. Diameters $\phi_{i,f}$ will, for example, be initialized respectively to the values corresponding to the value closest to the diameter of the spheres found when determining the target points. At each iteration (n), one begins by changing one of the helmet configurations, either by changing (step 10a) the treatment time for one of the shots, or by changing (step 10b) the diameter $\phi_{i,f}$ of a collimator. Preferably, at each iteration, steps 10a and step 10b are carried out alternately. More particularly, step 10a will be carried out by effecting a random selection of a number of shot i, and by randomly assigning a new treatment time to the corresponding variable TTi, for example by adding or removing a predetermined elementary time. Similarly, step 10b will be carried out by randomly choosing one of the numbers of shots i, by randomly selecting a number for beams f, and assigning to variable $\phi_{i,f}$ a given collimator diameter the value of which is randomly taken from among the different possible secondary collimator diameter values that can be used. In the aforementioned example of a radiosurgery device, given by way of illustration, the diameter values were 0 (plug), 4, 8, 14 or 18 mm. Once steps 10a or 10b have been carried out, a calculation is made, in step 11, of the variation in the objective function OF between the iteration (n) and the preceding iteration (n−1), and then, two successive tests are applied, namely, respectively, in an initial stage, steps 12 to 14 and, in a second stage, steps 15 to 16.

In steps 12 to 14, a test, commonly known as the 'Metropolis test' is applied to the objective function variation ΔOF, by calculating a probability P(ΔOF) according to the formula given in step 12 of the flow chart in FIG. 3. See, generally, Webb S. *Optimization by Simulated Annealling of three dimensional conformal treatment planning for radiation fields defined by a multi-leaf collimator*. Phys. Med. Biol. 36 1201–26,1991.

The step 13 test consists in comparing the probability P(ΔOF) calculated in step 12 with a figure of between 0 and 1 and taken at random at each iteration (n). If the probability P(ΔOF) is less than this randomly selected figure, the program branches directly to the second test, known as the 'end of optimization test' (step 15), without choosing the new configuration of the iteration (n) that had been changed by implementation of steps 10a or 10b. On the other hand, if the probability P(ΔOF) is greater than or equal to the figure taken at random, the new helmet configuration of the iteration (n) of steps 10a or 10b is accepted (step 14) and the program then goes on to step 15. The Metropolis test illustrated by steps 12 and 13 thus makes it possible, essentially, to determine whether, at a given iteration (n), the new helmet configuration that has been randomly determined in step 10a or 10b is chosen or not chosen.

The second test, in steps 15 and 16, consists in applying an optimization criterion the object of which is to determine automatically whether it is necessary to begin a new iterative dose calculation, or if it is, on the contrary, possible to halt the optimization process. In a precise example of embodiment, step 15 consists in comparing the value $OF^n$ of the objective function with a predetermined threshold. When the $OF^n$ value is below this threshold, the optimization criterion is satisfied, and the iterative calculation process is halted. On the other hand, when the $OF^n$ value is above the predetermined threshold, the optimization criterion is not fulfilled and a new iteration (n+1) is begun. More especially, knowing that, in the particular example of FIG. 3, the Metropolis test is applied to the objective function OF, prior to the new iteration (n+1), it is automatically checked (steps 17, 18, 19) to see whether it is necessary, as a preliminary, to reduce the control parameter T of the Metropolis test, by multiplying this parameter T, for example, by a coefficient α strictly contained between 0 and 1 and which is fixed, preferably, at 0.9. For this purpose, the number of iterations corresponding to a range of iterations during which parameter T has to be kept constant will have been fixed initially.

In another alternative embodiment, it is also possible to insert an additional test procedure (not shown) between steps 18 and 19 of the flow diagram in FIG. 3 which consists in automatically checking whether, over a given range of iterations, the different successive $OF^n$ values for the objective function that have been calculated have decreased at least once. If not, the optimization procedure is automatically halted. If so, the procedure is continued by going on to step 19, and by beginning a new iteration.

The optimum helmet configurations finally chosen are those for which the value of the objective function OF has been minimum at the time of iterative calculation.

The process according to the invention, whereof a preferred exemplary form of embodiment has just been described with reference to FIG. 3, can advantageously be implemented automatically by means of any suitably programmed computer. At the output, one automatically recovers one (single-target treatment plan) or several (multi-target treatment plan) helmet configurations (treatment time $TT_i$/ collimator diameter $\phi_{i,f}$), it being possible for the collimator diameters of a given helmet to be different and these diameters having been optimized by calculation so that the real irradiation dose subsequently delivered at each optimization point $M_p$ is as close as possible to the expected dose $ED_p$ at each of these points. As a result, the three-dimensional geometry of the irradiation dose that will be delivered is suited to the shape of the target volume, which advantageously makes it possible to reduce the number of shots, by comparison, for example, with treatment plans for which each helmet used at the time of a shot comprises only collimators of identical diameters.

On the basis of these helmet configurations automatically determined by calculation, the specialized operator can then, in a final stage not forming part of the process according to the invention, perform the treatment on the patient, fitting to the helmet of the radiosurgery device, between each shot, the secondary collimators that are of the appropriate diameter. This placing of the collimators on the helmet between each shot can also be automated, if necessary, by means of a robot

We claim:

1. Process for determining the configuration or configurations of a stereotactic radiosurgery helmet (5), to which can be fitted a plurality of collimators ($C_f$) focused on an irradiation isocenter, each helmet configuration subsequently corresponding to a shot (i) centered on a predetermined target point on a given target volume, characterized in that, on the basis:

of optimization points ($M_p$) chosen in relation to the target volume, of an expected irradiation dose ($ED_p$) at each optimization point ($M_p$), and of one (a single shot) or several (a series of successive shots) predetermined initial helmet configuration(s), the dose ($D_p$) received at each optimization point ($M_p$) is automatically optimized, through iterative dose calculation, by modifying, in the course of the successive iterations, the treatment time ($TT_i$) of at least one shot (i), and the diameter ($\phi_{i,f}$) of at least one collimator ($C_f$) used for at least one shot (i), and by calculating, at each iteration, an objective function (OF) having as variables the differences between the calculated dose ($D_p$) and the expected dose ($ED_p$) for each optimization point ($M_p$), iterative dose calculation being carried out automatically until the objective function (OF) satisfies a predetermined optimization criterion.

2. Process according to claim 1, characterized in that, at each new iteration, the treatment time ($TT_i$) of a single shot or the diameter ($\phi_{i,f}$) of a single collimator ($C_f$) used for a single shot (i) are changed alternately.

3. Process according to claim 2, characterized in that the choice, at each iteration, either of the shot (i) and of the associated new treatment time ($TT_i$), or of the shot (i), of the collimator ($C_f$) and of the associated collimator diameter ($\phi_{i,f}$) is carried out by random selection.

4. Process according to claim 1, characterized in that the value of the objective function ($OF^n$) at the iteration (n) is given by the following formula:

$$OF^n = \frac{1}{P}\sum_{p=1}^{P}[\,K_p(ED_p - D_p)^m\,]^{\frac{1}{m}}$$

wherein $K_p$ is a weighting factor, which is assigned to each optimization point $M_p$, P is the number of optimization points $M_p$, and m is positive, and is preferably equal to 2.

5. Process according to claim 1, characterized in that, at each iteration (n), the Metropolis test is applied to the objective function variation ($\Delta OF = OF^n - OF^{n-1}$); and:

if the Metropolis test is favorable, the helmet configurations of the iteration n are accepted;

then, the optimization criterion is applied; and:

if the optimization criterion is not satisfied, a new iteration (n+1) is begun starting from the helmet configuration or configurations of the preceding iteration (n−1) if the Metropolis test is unfavorable, or starting from the new helmet configuration or configurations determined at the iteration (n) if the Metropolis test is favorable.

6. Process according to claim 5, characterized in that the control parameter (T) used in the Metropolis test is constant for a predetermined number of iterations, termed the range of iterations, and in that, at the end of each range of iterations, the control parameter (T) used in the Metropolis test is reduced.

7. Process according to claim 6, characterized in that the reduction of the control parameter (T) of the Metropolis test is calculated by multiplying (T) by a factor ($\alpha$) of between 0 and 1, and, preferably, equal to 0.9.

8. Process according to claim 1, characterized in that the optimization criterion is satisfied when the objective function falls below a predetermined threshold.

9. Process according to claim 1, characterized in that the optimization criterion is satisfied when the objective function has not decreased over a range of iterations.

10. Process according to claim 8, characterized in that the helmet configuration or configurations finally chosen is/are that/those for which the value of objective function OF has been minimal at the time of iterative calculation.

* * * * *